United States Patent [19]
Ishii

[11] Patent Number: 5,801,266
[45] Date of Patent: Sep. 1, 1998

[54] METHOD FOR PRODUCING ACRYLONITRILE

[75] Inventor: Kanji Ishii, Kurashiki, Japan

[73] Assignee: Asahi Kasei Kogyo Kabushiki Kaisha, Japan

[21] Appl. No.: 913,347

[22] PCT Filed: Feb. 22, 1996

[86] PCT No.: PCT/JP96/00402

§ 371 Date: Aug. 27, 1997

§ 102(e) Date: Aug. 27, 1997

[87] PCT Pub. No.: WO96/26917

PCT Pub. Date: Sep. 6, 1996

[30] Foreign Application Priority Data

Feb. 28, 1995 [JP] Japan .................... 7-063534

[51] Int. Cl.⁶ ................................ C07C 253/00
[52] U.S. Cl. ................................ 558/320
[58] Field of Search ........................ 558/320

[56] References Cited

U.S. PATENT DOCUMENTS 3,649,179  3/1972  Ikeda et al. ............... 558/320

Primary Examiner—Joseph McKane
Assistant Examiner—Joseph Murray
Attorney, Agent, or Firm—Pennie & Edmonds LLP

[57] ABSTRACT

The present invention relates to a method for producing acrylonitrile comprising the steps of reacting propylene and/or propane, ammonia and molecular oxygen in the presence of a catalyst to form a reacted gas, contacting the reacted gas with a liquid containing water and an acid in a multi-stage quenching tower having three or more chambers and transferring the liquid contacted with the reacted gas in the second quenching chamber to the first quenching chamber. According to the present invention, high boiling point compounds are efficiently removed and clogging is prevented in an acrylonitrile recovery process so that the productivity of acrylonitrile is enhanced.

2 Claims, 1 Drawing Sheet

METHOD FOR PRODUCING ACRYLONITRILE

This application is a 371 of PCT/JP96/00402 filed Feb. 22, 1996, WO96/26917, Sep. 6, 1996.

TECHNICAL FIELD

The present invention relates to a method for producing acrylonitrile by ammoxydation, more particularly to a method for facilitating recovery of acrylonitrile by efficiently removing high boiling point compounds (heavies) and the like in the process of quenching a reacted gas.

BACKGROUND ART

The method for producing acrylonitrile by ammoxydation has been improved in various ways since its success in industrialization, and it is said that the method has technically matured. Still, efforts have been made to improve unit consumption of raw materials and utility, and to reduce production cost by achieving production efficiency.

It is well known that reacted gas obtained by reacting raw materials contains by-products such as hydrocyanic acid, acetonitrile and aldehyde in addition to acrylonitrile when acrylonitrile is produced by ammoxydation. The by-products react with acrylonitrile in the presence of unreacted ammonia or react with one another; as a result, high boiling point compounds are produced. The high boiling point compounds cause not only reduction in the yield of acrylonitrile, the target product, but also clogging at various places in towers in the subsequent processes. Consequently, the by-products must be immediately separated from the reacted gas.

Conventionally, a method has been adopted for separating unreacted ammonia in the form of a salt and simultaneously removing other impurities and the by-products mentioned above by preliminarily cooling the reacted gas produced in a reactor, then transferring the cooled reacted gas to a quenching tower immediately, and washing and quenching the reacted gas with water containing acids such as sulfuric acid. As one of the conventional methods, there is proposed a method employing a multi-stage quenching tower to divide a quenching process into two steps or more, which comprises separating most of the unreacted ammonia in the form of a salt by contacting the water containing a sufficient amount of sulfuric acid to neutralize the unreacted ammonia and simultaneously condensing a part of the water vapor contained in the reacted gas in the first chamber, and condensing most of the residual water vapor in the second chamber (U.S. Pat. No. 3,649,179).

This method has succeeded in reducing the cost for separating and treating the salt because of its higher concentration of the resultant ammonium salt than that in the conventional methods. Yet, the gas introduced from the first quenching chamber to the second quenching chamber contains unreacted ammonia, high boiling point compounds, polymers and scattered catalysts which are not removed in the first quenching chamber. A liquid containing high boiling point compounds, polymers, scattered catalysts and an ammonium salt is transferred in the form of mist together with the gas. Therefore, the liquid discharged from the second quenching chamber contains these impurities. To recover acrylonitrile contained in the discharged liquid, impurities should be removed.

Heretofore, the impurities contained in the discharged liquid was removed in an acrylonitrile recovery process or a waste water column; however, the impurities clogged a recovery column, a stripper and reboilers and pipes when the discharged liquid was transferred to the acrylonitrile recovery process. A large quantity of steam is required to transfer the discharged liquid to a waste water column for recovery of acrylonitrile from the discharged liquid. Therefore, the method was not economical.

Further, in the method of the above U.S. patent, if the liquid discharged from the second quenching chamber is sent back to the first quenching chamber in order to decrease the content of high boiling point compounds and the like in the discharged liquid, the same effect will be exhibited as in the case that a gas is treated in a one-stage quenching tower. In other words, the effect of the two-stage quenching tower cannot be obtained. Accordingly, the problems such as acrylonitrile loss and clogging due to high boiling point compounds have still remained.

DISCLOSURE OF THE INVENTION

The present inventors have made extensive and intensive research to solve the above problems and found that the high boiling point compounds are efficiently removed and that the clogging is effectively prevented by improving the treatment method of the liquid discharged from a quenching tower. As a result, they achieved the present invention.

This invention provides a method for producing acrylonitrile comprising the steps of reacting propylene, ammonia and molecular oxygen in the presence of a catalyst, contacting the reacted gas with liquid containing water and an acid in a multi-stage quenching tower having three or more chambers and supplying the liquid contacted with the reacted gas in the second quenching chamber to the first quenching chamber.

The quenching tower used in the present invention is a multi-stage quenching tower divided into three or more levels and each level consists of one chamber. One example of the tower of the present invention is shown in FIG. 1. If necessary, each chamber can be further divided into more than two levels. Packed beds for removing impurities and spray nozzles for supplying a liquid can be arranged in the quenching tower.

Hereinafter, an example of the production method of the present invention will be described referring to the multi-stage quenching tower of FIG. 1. The multi-stage quenching tower of FIG. 1 is divided into three levels. Namely, it comprises first, second and third quenching chambers (2), (3) and (4), respectively. The tower has a diameter of 2.5 to 3.0 m and a height of 12 to 14 m. The second and third quenching chambers have packed beds (21) and (22) packed with porcelain Raschig rings and spray nozzles on the end part of liquid supply pipes (7), (10) and (13), respectively.

The reacted gas obtained by reacting propylene, ammonia and molecular oxygen is first supplied to the first quenching chamber (2) through a gas leading pipe (1). In general, the composition of the reacted gas is as follows:

| <Component> | <vol. %> |
|---|---|
| acrylonitrile | 6.0–7.0 |
| ammonia | 0.0–1.0 |
| propylene and propane | 0.2–0.6 |
| acetonitrile | 0.1–0.5 |
| hydrocyanic acid | 0.8–1.6 |
| non-condensable gas | 60.0–67.0 |
| water vapor | 25.0–30.0 |
| other materials (acrolein, high boiling point compounds, etc.) | 0.0–0.2 |

This reacted gas is supplied to the first quenching chamber (2) at about 15 to 17 T/Hr and 230° to 280° C. "T" is defined as a measure of mass and 1T corresponds to 1000 kg. The reacted gas is cooled and washed by contacting it with the liquid containing water and an acid such as sulfuric acid.

The liquid is supplied to the first quenching chamber (2) through a liquid supply pipe (7) against the flow of the gas at 150 to 170 T/Hr. The temperature of the liquid is preferably between 85° and 95° C. The pH value of the liquid is preferably between about 5 and 6. The pH value can be adjusted by adding an acid to the liquid through an acid supply pipe (19). If necessary, the liquid may be cooled by a cooler (6).

Most of unreacted ammonia, high boiling point compounds, polymers, scattered catalysts and the like are removed in the first quenching chamber (2). The term "high boiling point compounds" means a nitrogen-containing hydrocarbon polymer produced in the reactor, polymers obtained by polymerizing acrolein, acrylonitrile or hydrocyanic acid, and polymers obtained by polymerizing β-aminopropionitrile obtained by reacting acrylonitrile and ammonia or cyanohydrin obtained by reacting acrolein and hydrocyanic acid.

The temperature of the liquid discharged through a discharging pipe (5) at the bottom of the quenching tower at the time when the inside of the first quenching chamber reaches its equilibrium state is 80° to 100° C. though it changes to some degree depending on the temperature and composition of the reacted gas supplied to the chamber. At that time, the liquid in the first quenching chamber (2) becomes a solution containing an extremely small amount of acrylonitrile, ammonium sulfate and viscous high boiling point compounds and so on. The liquid is discharged from the first quenching chamber (2) out of the tower through a liquid discharging pipe (14) at about 0.5 to 1.0 T/Hr. The pressure at the bottom of the tower is about 0.4 to 0.6 $kg/cm^2.g$.

The reacted gas treated in the first quenching chamber (2) is transferred to the second quenching chamber (3), and the removal of impurities left in the reacted gas is continued. The gas transferred from the first quenching chamber (2) to the second quenching chamber (3) contains unreacted ammonia, high boiling point compounds, polymers, a scattered catalyst and the like which are not removed in the first quenching chamber (2). A liquid containing high boiling point compounds, polymers, scattered catalysts and ammonium sulfate is entrained with the gas in the form of mist.

In the second quenching chamber (3), the reacted gas may be treated according to the same method as the first quenching chamber (2) or by the conventional methods. For example, the liquid supplied to the second quenching chamber (3) is cooled down to 68° to 73° C. by a cooler (9) and supplied into the chamber through a liquid supply pipe (10) at 150 to 170 T/Hr. If necessary, an acid can be supplied through an acid supply pipe (20).

In this chamber, the above-mentioned impurities remaining in the reacted gas are removed, and the water vapor initially contained in the reacted gas is partially liquefied by the condensation. Therefore, the amount of liquid increased thereby is discharged from this chamber (3).

In the present invention, the liquid discharged from the second quenching chamber (3) through a liquid discharging pipe (8) is supplied into the first quenching chamber (2) through a liquid supply pipe (15). In addition, the discharged liquid also can be supplied to an acrylonitrile recovery process through a liquid discharging pipe (16). The amount of liquid supplied from the second quenching chamber (3) into the first quenching chamber (2) is preferably 10 to 60 wt. %, more preferably 30 to 50 wt. %, of the total amount of the liquid supplied from the second quenching chamber (3) to the first quenching chamber (2) and the liquid supplied from quenching chambers above second quenching chamber (3) to an acrylonitrile recovery process, which corresponds to the total amount of the liquid supplied from the water discharging pipes (16) and (17).

The temperature of the liquid discharged from the second quenching chamber (3) at the time when the inside of the second quenching chamber (3) reaches its equilibrium state is between 70° and 90° C. though it changes to some degree depending on the temperature, composition of the reacted gas transferred in the chamber and the load of the cooler (9). The liquid is discharged from the chamber at about 0.5 to 2.7 T/Hr. The pressure at the bottom of the second quenching chamber is about 0.3 to 0.6 $kg/cm^2.g$.

The gas treated in the second quenching chamber (3) is transferred to the third quenching chamber (4). The transferred gas contains only a very small quantity of the impurities mentioned above. In the third quenching chamber (4), the reacted gas also can be treated according to the same method as the first quenching chamber or by conventional methods. For example, the liquid is discharged through a liquid discharging pipe (11) and cooled down to about 36° to 38° C. by a cooler (12), transferred from spray nozzles through a liquid supply pipe (13), and supplied to the chamber at 60 to 80 T/Hr. If necessary, an acid can be added to the liquid again.

The temperature of the discharged liquid at the time when the inside of the third quenching chamber reaches its equilibrium state is between 60° to 80° C. though it changes to some degree depending on the temperature, composition of the reacted gas transferred in the chamber and the load of the cooler (12). The liquid is discharged from the third quenching chamber (4) at about 2 to 4 T/Hr. The pressure at the bottom of the third quenching chamber (4) is about 0.3 to 0.5 $kg/cm^2.g$.

The amount of the water vapor to be condensed in each quenching chamber can be adjusted by changing a load of coolers to control the temperature of the gas transferred to the following chamber or process.

The reacted gas, from which high boiling point compounds and the like are removed in a multi-stage quenching tower, is transferred to a process for recovering acrylonitrile. The liquid discharged from the third quenching chamber (4) out of the tower through a liquid discharging pipe (17) can be recycled after recovering acrylonitrile contained in the liquid.

Hereinafter, the process for recovering acrylonitrile will be described. The gas contains acrylonitrile, acetonitrile, hydrocyanic acid, carbon dioxide, carbon monoxide, nitrogen, unreacted propane and unreacted propylene and so on, and the temperature of the reacted gas passing through a gas transferring port (18) is between about 37° and 39° C. The gas is transferred to an absorption column to absorb acrylonitrile, hydrocyanic acid, acetonitrile and the like into water. The gas which is not absorbed in the absorption column is incinerated or emitted in the air, if necessary, after purification.

The liquid discharged from the bottom of the absorption column is transferred to the acrylonitrile recovery column together with the liquid discharged through liquid discharging pipes (17) and (16).

In the recovery column, acetonitrile is removed by extractive distillation using water as an extractant. From the top of the column, the liquid containing acrylonitrile, hydrocyanic acid and a small amount of water is discharged and transferred to the purification process for acrylonitrile. The liquid discharged from the bottom of the column is transferred to a stripper to remove acetonitrile.

The acrylonitrile recovery column and the stripper are both equipped with reboilers. The liquid discharged from the bottom of the tower is supplied to the reboilers. Further, steam is supplied to the reboilers while the liquid is circulated to remove acrylonitrile, hydrocyanic acid, acetonitrile and the like.

According to the present invention, the high boiling point compounds are efficiently removed and clogging is prevented in an acrylonitrile recovery process so that the productivity of acrylonitrile is enhanced.

Figure 1:
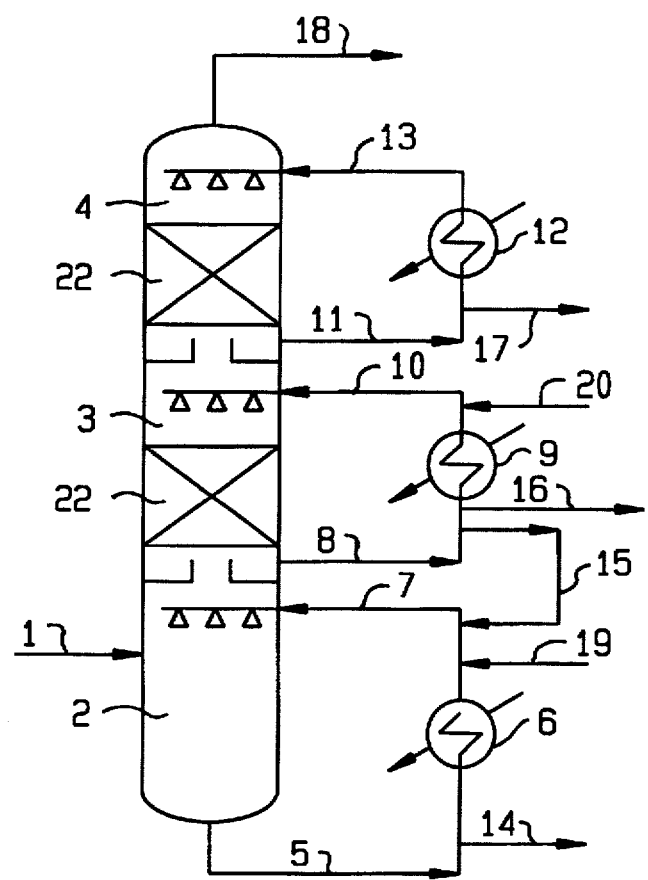
FIG. 1 is a schematic view of the multi-stage quenching tower used in the present invention.

Description of Numerals
1: gas lead in pipe
2: first quenching chamber
3: second quenching chamber
4: third quenching chamber
5: liquid discharging pipe
6: cooler
7: liquid supply pipe
8: liquid discharging pipe
9: cooler
10: liquid supply pipe
11: liquid discharging pipe
12: cooler
13: liquid supply pipe
14: liquid discharging pipe out of the tower
15: liquid supply pipe
16: liquid discharging pipe oui,. of the tower
17: liquid discharging pipe out of the tower
18: gas transferring port
19: acid supply pipe
20: acid supply pipe
21: packed bed
22: packed bed

BEST MODE FOR CARRYING OUT THE INVENTION

[Measurement of concentration]

In each Example, the concentrations of high boiling point compounds and ammonium sulfate remaining in the liquid after contacting reacted gas and the liquid were measured according to the following method.

The sample liquid taken out from each quenching chamber was evaporated under a warm bath of 90° C., dried at 105° C. and allowed to cool in a desiccator. The residue was dissolved into warm water at 40° C., and the amount of ammonium sulfate was measured by a formaldehyde method. The formaldehyde method is a measuring method comprising adding formaldehyde to ammonium sulfate, and titrating the generated sulfuric acid by alkali.

The concentrations of high boiling point compounds and ammonium sulfate were calculated by applying the amount of the sample and the amount of the residue (the total amount of the dried high boiling point compounds and ammonium sulfate) to the following formula. The amount of the high boiling point compounds was calculated by subtracting the amount of ammonium sulfate from the amount of the above mentioned residue.

$$C(wt. \%) = (T/S) \times 100$$

C: concentration of the total amount of high boiling point compounds and an ammonium sulfate
T: total amount of dried high boiling point compounds and dried ammonium sulfate
S: amount of the sample obtained Further, the concentration of acrylonitrile was measured by a gas chromatography.

<EXAMPLE 1>

An experiment was carried out using the multi-stage quenching tower whose inside was divided into three levels as disclosed in FIG. 1. The quenching tower had a diameter of 2.7 m and a height of 12.7 m. In each quenching chamber of the tower, spray nozzles were arranged on the end part of liquid supply pipes. The packed beds (21) and (22) of the second quenching chamber (3) and the third quenching chamber (4) were filled with porcelain Raschig rings.

Propylene, ammonia and air were reacted in a reaction tower to obtain a reacted gas with the composition as follows:

| <Component> | <vol. %> |
|---|---|
| acrylonitrile | 6.5 |
| ammonia | 0.5 |
| propylene and propane | 0.4 |
| acetonitrile | 0.3 |
| hydrocyanic acid | 1.2 |
| non-condensed gas | 63.5 |
| water vapor | 27.5 |
| other materials (acrolein & high boiling point compound) | 0.1 |

The reacted gas was introduced through the gas lead in pipe (1) into the first quenching chamber (2) at 15 T/Hr. The temperature of the gas was 250° C.

The liquid discharged from the bottom of the first quenching chamber (2) and the second quenching chamber (3) at 90° C., and containing sulfuric acid which was added to adjust the pH value of the liquid to 5.3, was supplied through a liquid supply pipe (7) to the first quenching chamber (2) at 160 T/Hr. The liquid contacted with the gas was circulated through the liquid discharging pipe (5) and the liquid supply pipe (7) and supplied to the quenching chamber. The liquid was discharged from the first quenching chamber (2) to the outside of the tower through the liquid discharging pipe (14) at 0.8 T/Hr.

The reacted gas treated in the first quenching chamber (2) was transferred to the second quenching chamber (3). The liquid of 70° C., whose pH value was adjusted to 5.5 with sulfuric acid, was supplied at 160 T/Hr. The liquid contacted with the gas was circulated and supplied in the same way as in the first quenching chamber (2). The liquid was discharged from the second quenching chamber (3) at 1.8 T/Hr and supplied to the first quenching chamber (2) through a liquid supply pipe (15).

The reacted gas treated in the second quenching chamber (3) was transferred to the third quenching chamber (4). The liquid of 37° C., whose pH value was 5.5, was supplied at 70 T/Hr. The liquid contacted with the gas was circulated and supplied in the same way as in the first quenching chamber. The liquid was discharged from the third quenching chamber (4) at 2.7 T/Hr and sent to the acrylonitrile recovery process.

The concentrations of high boiling point compounds, ammonium sulfate and acrylonitrile, which remain in the liquid discharged from each chamber at the time when the inside of the multi-stage quenching tower reached its equilibrium state, are shown in Table 1.

In the acrylonitrile recovery process, the reboilers arranged in the acrylonitrile recovery column and the stripper were operated without cleaning their insides for a year. When the insides of the column and the stripper were inspected after one-year operation, no polymer and the like were observed.

<COMPARATIVE EXAMPLE 1>

The reacted gas with the composition shown in Example 1 was treated in the same manner as in Example 1 except that the liquid was supplied to the acrylonitrile recovery process without supplying the liquid to the first quenching chamber (2).

The reboilers in the acrylonitrile recovery column and the stripper clogged after 4.5 month and 3 month operation, respectively. The reboilers needed cleaning.

Industrial Application

According to the method of the present invention, problems such as clogging caused by high boiling point compounds or polymers can be avoided in an acrylonitrile recovery process. As a result, the productivity of acrylonitrile can be increased.

TABLE 1

|  | 1st quenching chamber | 2nd quenching chamber | 3rd quenching chamber |
| --- | --- | --- | --- |
| high boiling point compounds (wt. %) | 18.4 | 3.5 | 0.2 |
| ammonium sulfate (wt. %) | 28.0 | 0.8 | 0.01 |
| acrylonitrile (wt. %) | 0.08 | 0.8 | 5.2 |

What is claimed is:

1. A method for producing acrylonitrile in the presence of a catalyst comprising: reacting ammonia, molecular oxygen, and at least one reactant chosen from the group consisting of propylene and propane to form a reacted gas; contacting the reacted gas with a liquid containing water and an acid in a multi-stage quenching tower comprising at least three quenching chambers, a first quenching chamber located at the base of the quenching tower, a second quenching chamber located immediately above the first quenching chamber and a third quenching chamber located immediately above the second quenching chamber; and transferring the liquid in contact with the reacted gas in the second quenching chamber to the first quenching chamber.

2. The method for producing acrylonitrile according to claim 1, wherein an amount of the liquid in contact with the reacted gas in the second quenching chamber transferred to the first quenching chamber is 10 wt. % to 60 wt. % of the amount of the liquid supplied from liquid discharging pipes discharging liquid from the quenching chambers above the first quenching chamber plus the amount of liquid supplied from the second quenching chamber to the first quenching chamber.

\* \* \* \* \*